United States Patent
Kelly et al.

(10) Patent No.: US 6,501,076 B1
(45) Date of Patent: Dec. 31, 2002

(54) ELECTRON ANALYZER HAVING AN INTEGRATED LOW PASS FILTER

(75) Inventors: Michael A. Kelly, Portola Valley, CA (US); Charles S. Bryson, III, Santa Clara, CA (US)

(73) Assignee: FEI Company, Hillsboro, OR (US)

( * ) Notice: Subject to any disclaimer, the term of this patent is extended or adjusted under 35 U.S.C. 154(b) by 84 days.

(21) Appl. No.: 09/687,261

(22) Filed: Oct. 11, 2000

(51) Int. Cl.[7] ............................................. H01J 49/46
(52) U.S. Cl. ...................... 250/305; 250/396; 250/281; 250/396 R; 250/296
(58) Field of Search ............................. 250/306, 396, 250/305, 281, 294, 311, 396 R, 297, 296

(56) References Cited

U.S. PATENT DOCUMENTS

| | | | |
|---|---|---|---|
| 5,166,519 A | * 11/1992 | Turner | 250/305 |
| 5,321,262 A | * 6/1994 | Turner | 250/305 |
| 5,583,336 A | 12/1996 | Kelly | 250/305 |
| 5,969,354 A | * 10/1999 | Kelly | 250/305 |

* cited by examiner

*Primary Examiner*—Bruce Anderson
*Assistant Examiner*—Zia R. Hashmi
(74) *Attorney, Agent, or Firm*—Michael O. Scheinberg (57) ABSTRACT

An electron energy analyzer integrated with a low-pass energy filter. The electron energy analyzer includes a separation region disposed inside a coil creating a magnetic field parallel to an axis of the separation region. The magnetic field is terminated at both ends of the separation region and shunted by a magnetic yoke around the outside of the coil. Electrons entering the separation region at a polar angle with respect to the axis accumulate an azimuthal angle dependent on the energy of the electron. Thereby, the direction the electron is traveling when it exits the separation angle depends upon its energy. According to the invention, a low-pass reflector is positioned at the input side of the analyzer, for example, a grounded grid in back of which is positioned a negatively biased absorption electrode. Electrons having energy exceeding the electrode bias are absorbed. Electrons having energy less than the electrode bias are reflected and exit the reflector with the same energy as before. The reflector may be curved to focus the electrons. A curved reflector may be used to introduced chromatic dispersion in the electron beam so that electrons of different energies enter the analyzer at different polar angles. A second reflector may be positioned on the other end of the analyzer so that the energy-analyzed electrons are extracted on the input side of the analyzer.

18 Claims, 6 Drawing Sheets

ELECTRON ANALYZER HAVING AN INTEGRATED LOW PASS FILTER

FIELD OF THE INVENTION

The invention relates generally to generally to devices for separating electrons or other charged particles according to their energies. Specifically, the present invention relates to real-time analysis of the low-energy portion of the energy distribution of such particles.

BACKGROUND ART

Figure 1:
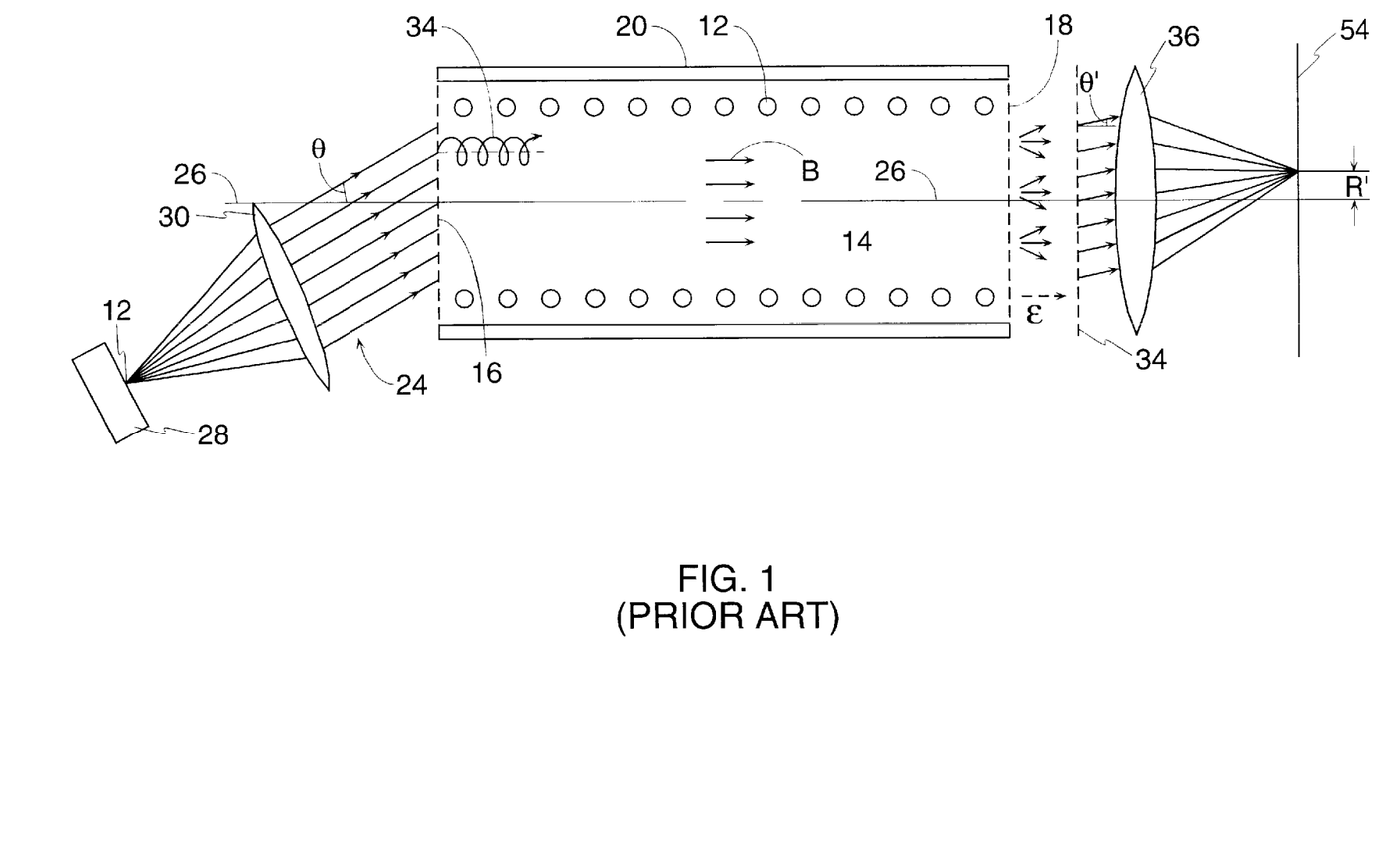
FIG. 1 is a schematic side view, partially in cross section, of a prior-art electron analyzer.

Kelly in U.S. Pat. Nos. 5,583,336 and 5,969,354 describes an electron analyzer for the real-time detection of the entire energy distribution of a beam of electrons. Both these patents are incorporated herein by reference in their entireties. The analyzer of the '336 patent is illustrated in FIG. 1. Its central part is an energy separator 10 that uses a solenoid 12 powered by an unillustrated DC current supply to create a substantially uniform magnetic field B in a separation region 14. The magnetic field is terminated by magnetic meshes 16, 18 linked by cylindrical magnetic yoke 20. The '354 patent generalizes this configuration to non-uniform magnetic fields and magnetic meshes acting as lenses.

A collimated electron source beam 24 is offset by a polar angle $\theta$ from a longitudinal axis 26 of the energy separator 12. It is assumed that the azimuthal angle $\phi$ lies within the plane of the illustration, which corresponds to a value of zero. The source beam 24 originates from an electron source 28 and is collimated by a set of beam optics 30.

It is well known that a charged particle entering a magnetic field region at an oblique angle to the magnetic field, here parallel to the central axis 26, will gyrate about the local magnetic field line B in a helical path 32 so as to maintain its polar angle $\theta$ but to have its azimuthal angle $\phi$ with respect to the local magnetic field line B increasing linearly with time or distance with the proportionality constant dependent upon magnetic field and the particle's kinetic energy and charge. These two angles $\theta$ and $\phi$ determine the instant velocity of the charged particle with respect to the central axis 26. Assuming the same initial polar and azimuthal angles $\theta_0$ and $\phi_0$ for all energies, the total angular rotation $\Delta\phi$ will depend upon the particle's energy. As a result, electrons of differing energies and all entering the separator 10 with the same polar angle $\theta_0$ and the same azimuthal angle $\phi_0$ will exit the separator on a path at an angle dependent upon the electron energy. In fact, the polar angles will all be the same $\theta$ but the azimuthal angles $\phi$ will be energy dependent. If only a limited energy range is being analyzed, a distribution of the electrons as a function of the exit azimuthal angle $\phi$ will give the energy distribution. However, for larger energy ranges it is necessary to resolve the uncertainty in multiples of $2\pi$ in the azimuthal angle. This is accomplished with electrostatic biasing between the exit magnetic grid 18 and an electrical grid 34 which provides an energy dependent change of the polar angle $\theta$.

Figure 2:
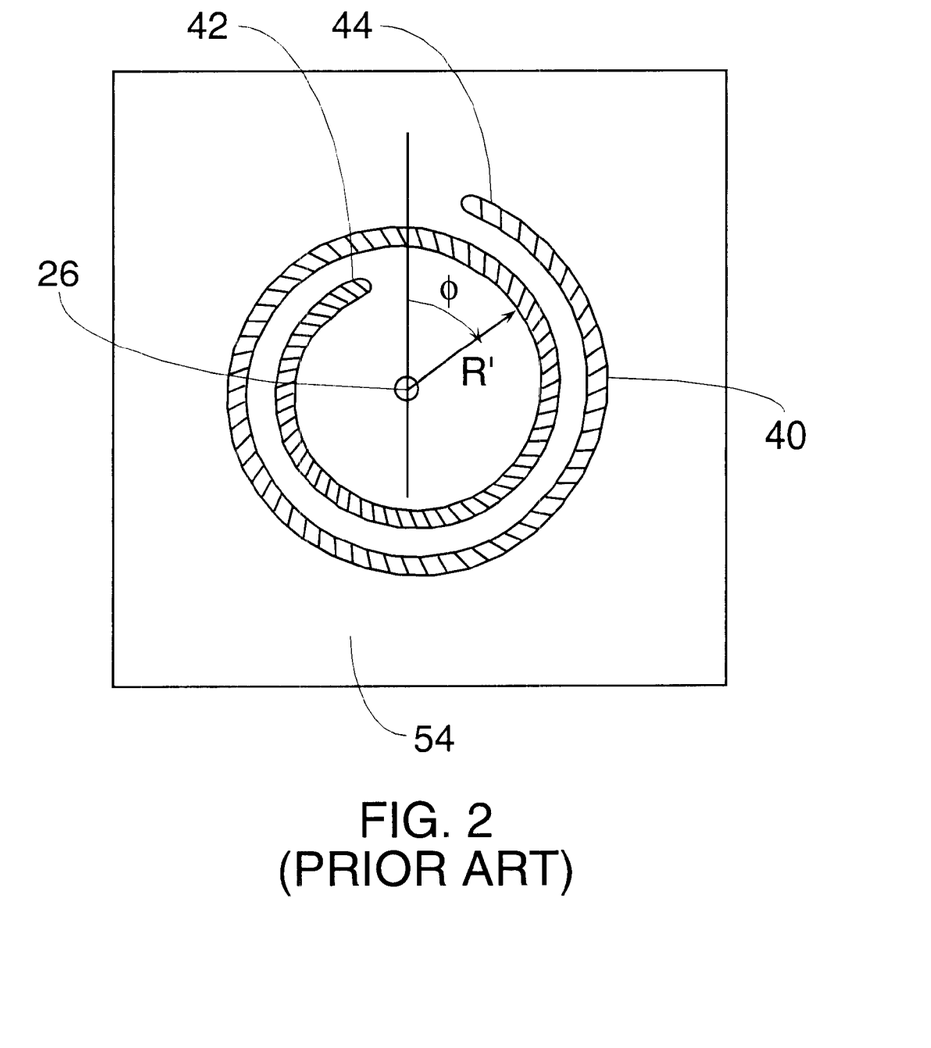
FIG. 2 is a schematic plan view of an imaging detector used in the analyzer of FIG. 1.

Beam optics 36 focus the electrons on an imaging screen 38 or other radiation detector arranged in two dimensions, for example, a 2-dimensional CCD imaging array. As illustrated in FIG. 2, the electrons will fall along a spiral locus 40 with its two ends 42, 44 defining the two limits of the detected energy range and the portions in between having a one-to-one correspondence to intermediate energies. The distribution of intensities along the spiral locus 40 corresponds to the energy distribution of the electrons.

One intended use of the energy analyzer of FIG. 1 is as the analyzer for an Auger electron spectrometer. Auger spectrometers are commercially available from several sources, including Physical Electronics (PHI), a division of Perkin-Elmer of Eden Prairie, Minnesota, Vacuum Generators of the United Kingdom, and Omicron of Delaware.

In the typical practice of Auger spectroscopy, the solid is probed with a beam of primary electrons in the low keV range of energies and produces a secondary electron through an Auger transition process having a well defined Auger energy $E_{AUGER}$. In Auger spectroscopy, the probing radiation ejects an inner-shell electron from an atom. Then in the Auger transition, a first outer-shell electron falls into the inner-shell vacancy and a second outer-shell electron is ejected carrying the difference in energy. The spectrometer analyzes the energy of the ejected electron as the Auger energy $E_{AUGER}$. Auger energies are generally in the range of a few hundred eV to a few keV for the typical practice of Auger electron spectroscopy. The Auger energy $E_{AUGER}$ is for the most part unique for each atom, primarily dependent upon the atomic number Z but also depends on the bonding with neighboring atoms. Thus, the measured electron energy can be used to determine the composition of the material, at least near its surface. Auger electron spectroscopy allows the very quick and highly accurate measurement of film thicknesses up to about 20 nm.

Auger energies are typically in the range of a few hundreds to a few thousands of electron volts (eV). Because of the multiple electron transitions, the Auger energy is typically less than half of the primary energy $E_p$. Further, to enhance the Auger signal, the primary energy $E_p$ is increased even more, often to five times the Auger energy.

Auger signals are generally relatively weak compared to the primary beam. Also, other processes can occur as the primary beam propagates into the material. As a result, the Auger signal is often difficult to extract from a greater number of electrons at the same energy. In addition, electrons of higher energy leave the surface, and these electrons can degrade the analysis system. Nonetheless, the electron analyzer of FIGS. 1 and 2 must be designed to accurately treat all energies of electrons incident upon it even though when used in an Auger spectrometer only the lower energies are of interest.

Accordingly, it is desired to provide an electron spectrometer that can more effectively and accurately determine the energies of the lower-energy portion of an energy distribution. It is further desired to integrate such means with the energy analyzer of FIG. 1 with the addition of only a few elements.

SUMMARY OF THE INVENTION

The invention includes a low-pass energy filter on the input to an energy analyzer for charged particles.

The invention includes an electron energy analyzer including a reflector positioned at the input acting as a low-pass filter. The reflector includes a grid held at a predetermined potential, preferably grounded, and an electrode disposed in back of it held at a more positive potential and configured to reflect electrons with a lower potential energy than the negative electrode potential. These electrons with less energy are reflected and accelerated back through the front grid electrode.

The plane of the reflector is inclined to the analyzer axis so that low-energy electrons reflected from the low-pass filter enter the analyzer at an oblique angle. The analyzer is preferably composed of a drift region having an axial magnetic field around which the energies gyrate in a spiral pattern. The amount of rotation accumulates along the drift region and depends upon the electron energy.

In one embodiment, the reflector is planar. A collimated beam striking the reflector is collimated upon entering the drift region.

In a second embodiment, the reflector is also planar but receives a beam from a light source having its energy components being angularly dispersed so that the components enter the drift region with an energy-dependent oblique angle.

In a third embodiment, the reflector is curved, preferably parabolically or as a paraboloid so as to both energy filter and collimate the beam entering the drift region.

In a fourth embodiment, a second electron reflector is positioned at the end of the drift region opposite the input end, and the electrons are extracted from the input side of the drift region.

DETAILED DESCRIPTION OF THE PREFERRED EMBODIMENTS

Figure 3:
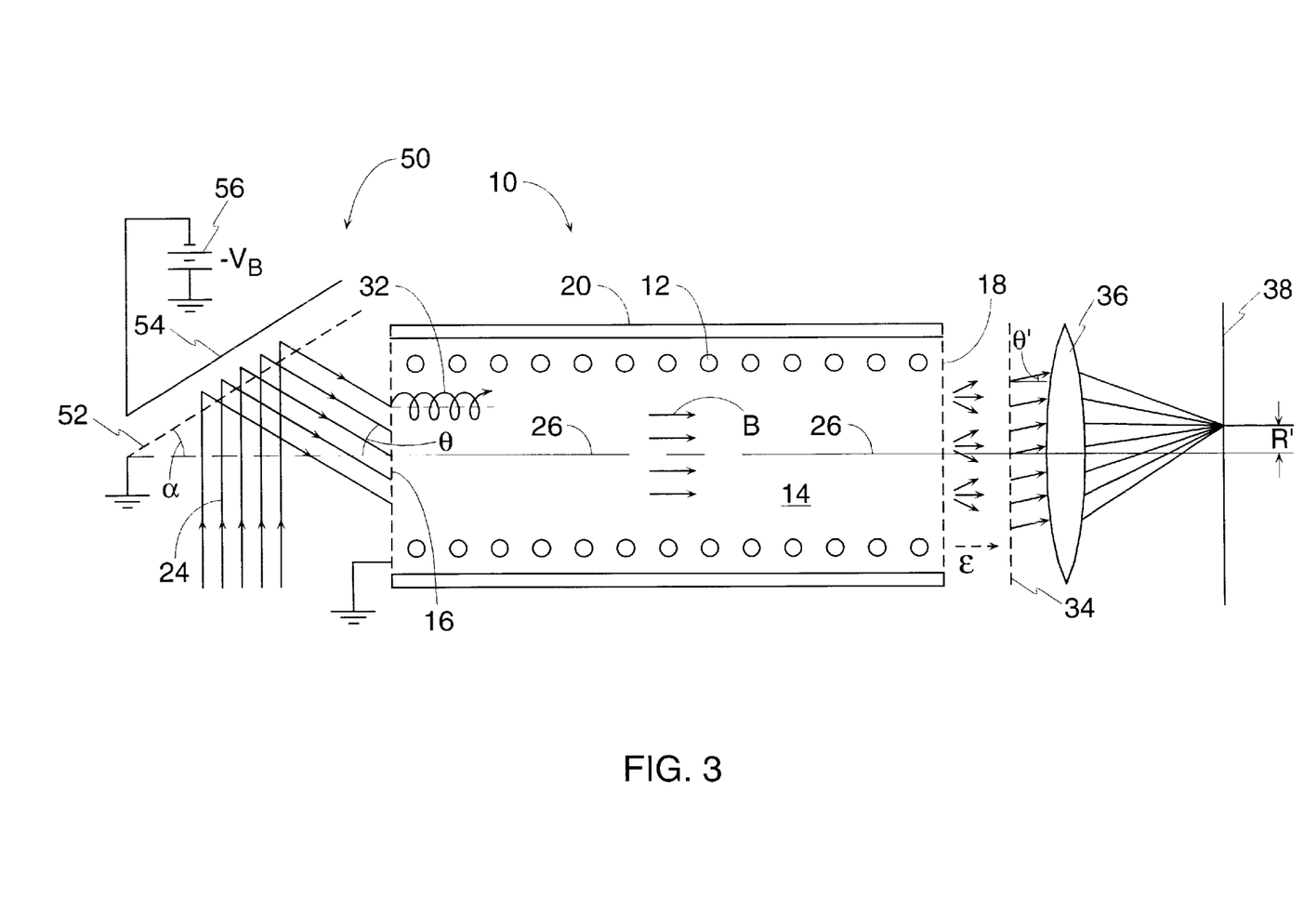
FIG. 3 is a schematic side view, partially in cross section, of a first embodiment of an electron analyzer of the invention with an integrated low-pass filter formed of a flat reflector.

The invention includes a low-pass energy filter integrated with an electron analyzer. A first embodiment of the invention is illustrated in the schematic cross-sectional view of FIG. 1. The electron energy separator 10 is much the same as that illustrated in FIG. 1. However, the collimated input beam 24 is incident upon a low-pass reflector 50, which includes a grounded grid 52 and a biased absorption electrode 54. The absorption electrode 54 needs to act as a beam dump. It may consist of a metal plate coated with graphite, or it may include a transparent biased grid with a more positively biased plate in back of it. The region between the grounded reflector grid 52 and the grounded magnetic input grid 16 is substantially free of electric as well as magnetic fields, thus allowing the relatively low energy electrons to propagate in this region without deflection.

In this embodiment, the grid 52 and absorption electrode 54 are flat and separated by a constant gap. The grid 52 and electrode 54 are set with their planes at an oblique angle α to the axis 26 of the analyzer and are also set at an oblique angle to the input beam 24. In the simple illustrated configuration in which the input beam 24 is perpendicular to the axis 26 of the analyzer, $$\theta = \frac{\pi}{2} - 2\alpha.$$

A DC power supply 56 biases the absorption electrode 54 at a negative voltage $-V_B$ relative to the grounded grid 52. The relative bias creates within the gap an electric field which retards the electrons approaching the absorption electrode 54. However, the retardation occurs only in the direction normal to the gap. The electrons retain their velocity in the direction parallel to the plane of the gap. That is, let the electron energy E be the sum of energies $E_1$ and $E_2$ perpendicular and parallel to the gap, which are related by $$E_1 = E \sin\alpha$$

and $$E_2 = E \cos\alpha.$$

The parallel energy $E_1$ is conserved, but the perpendicular energy $E_2$ is retarded. If $E_2$ is greater than $eV_B$, the electron will reach the absorption electrode 54 and be absorbed there, assuming the absorption electrode 54 has been designed to minimize reemission. On the other hand, if $E_2$ is less than $eV_B$, it will never reach the absorption electrode 54 but will be momentarily stopped in the gap and then repelled by the more negatively charged absorption electrode 54 back across the gap and out through the grid 52. Upon exiting the grid 52, it will have the same energy E as before but following a different angle of travel. The reflector 50 therefore operates as a low-pass energy filter with a low-pass energy $E_{LP}$ of $$E_{LP} = \frac{eV_B}{\cos\alpha}.$$

As a result, only the low-energy portion of the input beam 24 enters the energy separator 10.

The exclusion of high-energy electrons from the analyzer provides a number of advantages. In Auger and related spectroscopy, the electrons of interest have lower energies and are significantly fewer than higher-energy electrons, such as the primary electrons producing the Auger interaction. If the high-energy electrons are eliminated prior to analysis and detection, noise associated with the high-energy electrons is significantly reduced. Furthermore, since only a restricted azimuthal range Δφ is being detected, it is possible to eliminate the, uncertainty with factors of 2π in Δφ. Therefore, the additional discrimination in θ provided by the biased exit grid 34 may not be necessary, and this grid 34 may be eliminated.

Figure 4:
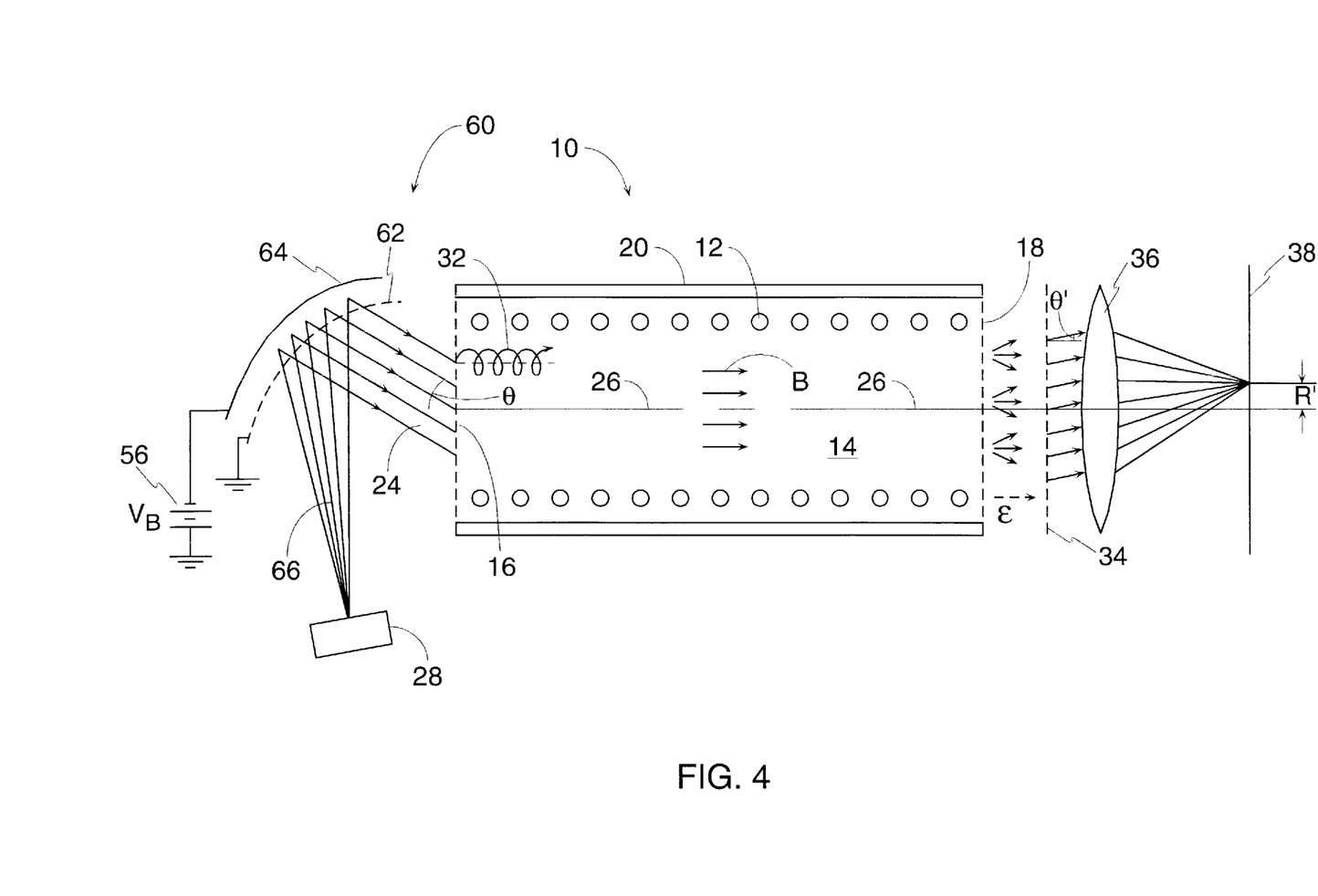
FIG. 4 is a schematic side view, partially in cross section, of a second embodiment of an electron analyzer of the invention having a low-pass filter formed of a curved reflector which also operates as a lens.

The reflector can have a more complex shape than that illustrated in FIG. 3 and can perform additional functions. For example, as illustrated in FIG. 4, a parabolic reflector 60 includes a grid 62 and an electrode 64 both of which are either right parabolically shaped (shaped only in one dimension) or shaped in two dimensions as paraboloids with a nearly constant gap between them. The parabolic shaping allows the low-pass reflector 60 to additionally act as a lens collimating a divergent source beam 66 into a well collimated input beam 24. Generally, such shapes are optimized for minimum dispersion of the reflected electrons. Right parabolically shaped grids and electrodes, that is, shaped in only one dimension, focus only in one dimension, but they are easy to fabricate. Full collimation of the input beam 24 would require additional beam optics effective in the other dimension. Paraboloids, because they are shaped in two dimension, focus in two dimensions but are more difficult to accurately fabricate, especially for transparent grids. Round or spherically shaped reflectors are easier to form than parabolically shaped ones but do not focus as accurately.

The previous embodiments have assumed or accomplished minimum chromatic dispersion in the input beam, that is, electrons of all energies are traveling along parallel paths upon entering the analyzer. In some situations, on the other hand, it is advantageous to maximize the chromatic dispersion on the input to provide an additional energy discrimination by making the polar angle θ at the entrance to analyzer depend upon the electron energy. Such an analyzer with low-pass filter is illustrated in the schematic illustration of FIG. 5. A source beam 70 is assumed to be collimated before it enters a curved reflector 72 having a curved biased electrode 74 separated from a curved grounded grid 76 by a gap that is a significant fraction of the radius of curvature of the electrode 74 and grid 76.

Figure 5:
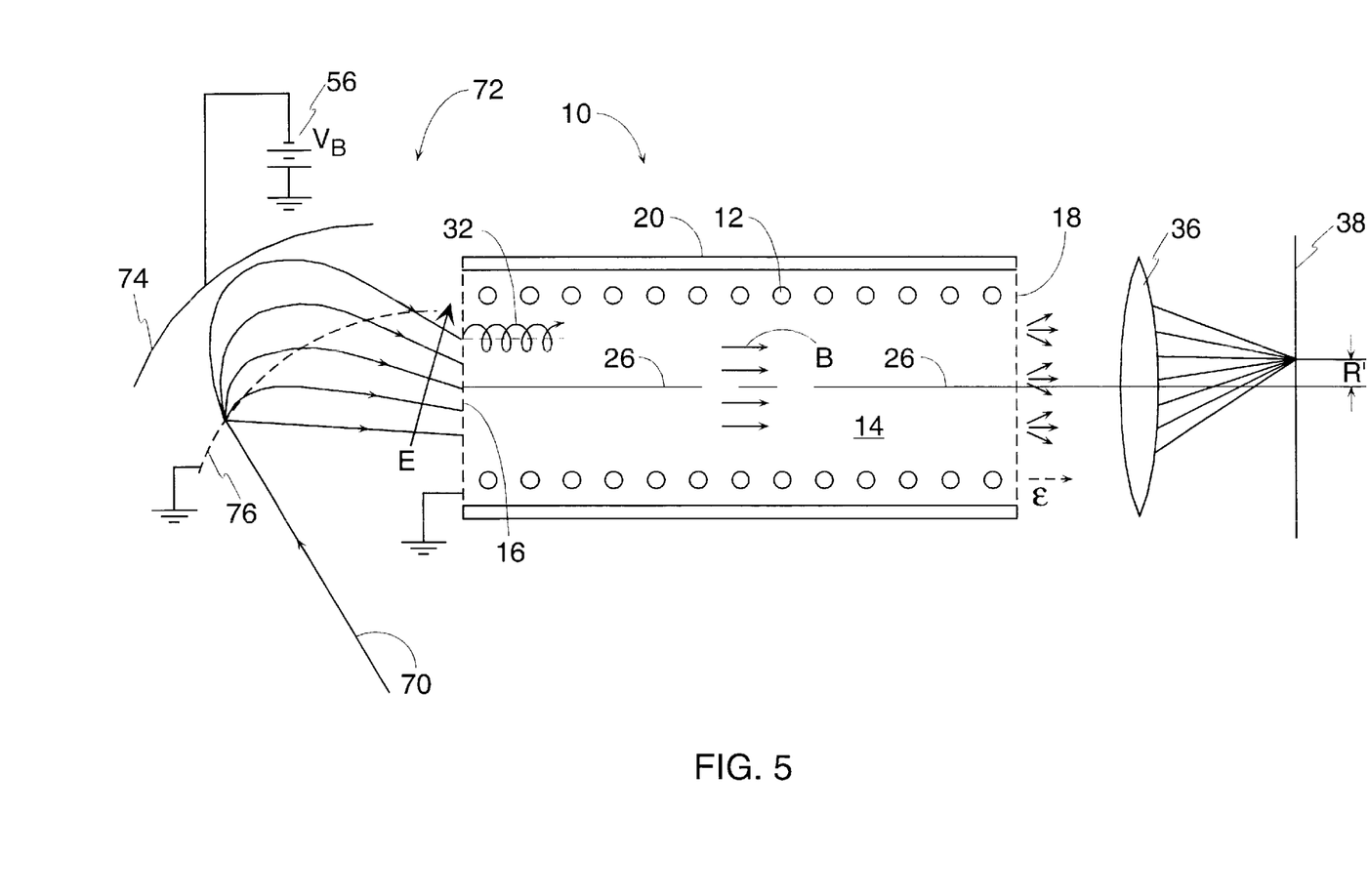
FIG. 5 is a schematic side view, partially in cross section, of a third embodiment of an electron analyzer of the invention having a low-pass filter formed of a flat reflector and positioned to also angularly disperse the energy components.

The curved reflector 72 acts not only as a low-pass filter but also chromatically disperses the reflected low-energy electrons. As a result, the low-energy electrons enter the energy separator 10 at polar angles θ dependent upon the electron energy E.

The different polar angles θ are maintained through the energy separator 10 as the electrons accumulate different amounts of the azimuthal angle φ dependent upon their energy. Therefore, as the electrons emerge through the exit mesh 18, they are discriminated in both θ and φ according to their energy. As a result, the additional energy-dependent θ discrimination provided by the biased mesh 34 of FIG. 1 is not required in this embodiment, and the electrons may be directly focused by the exit beam optics 36. According to Kelly's '354 patent, the exit beam optics may be implemented by curving the exit mesh 18.

Figure 6:
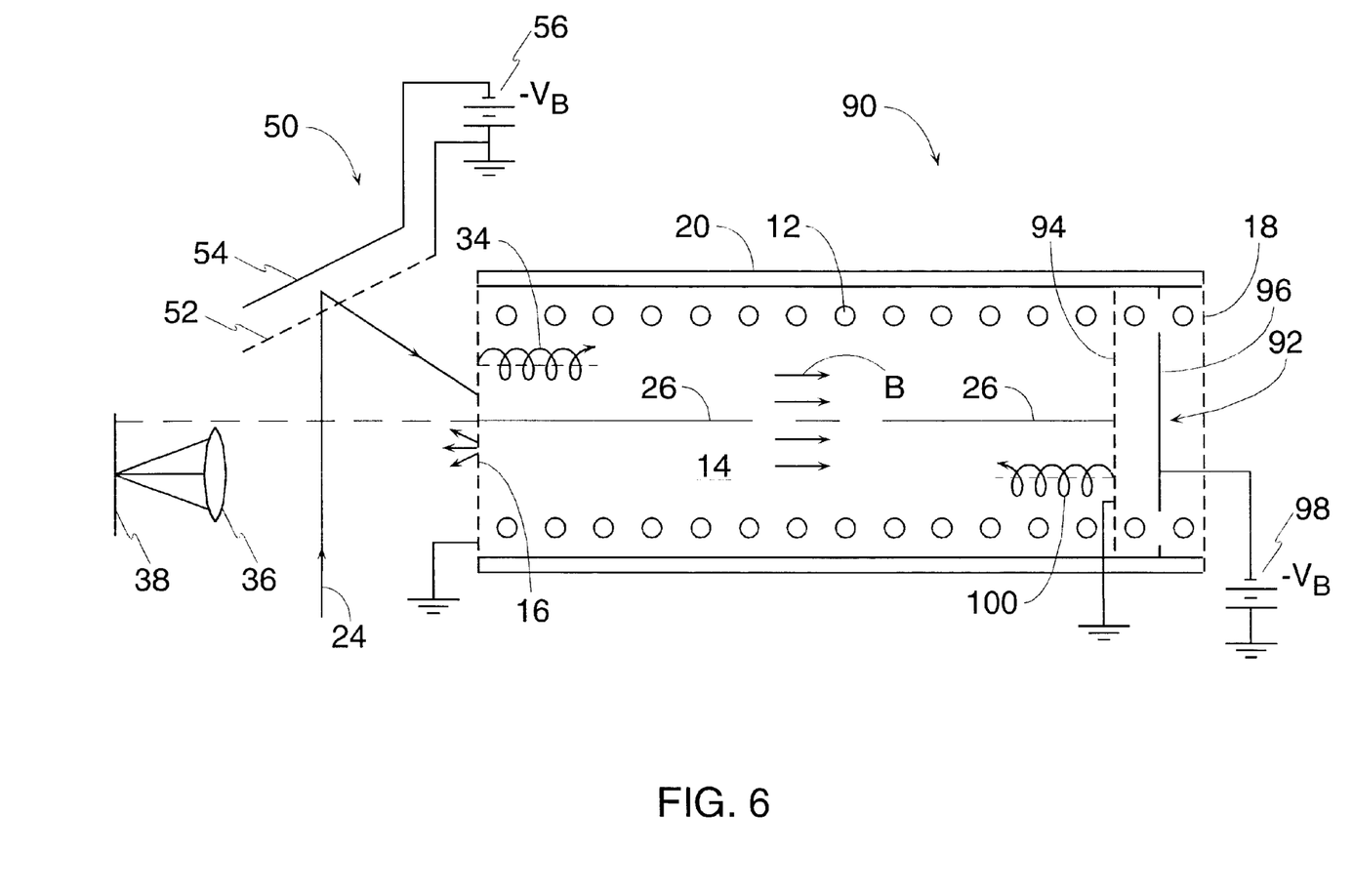
FIG. 6 is a schematic side view, partially in cross section, of a fourth embodiment of an electron analyzer of the invention having input and extraction at the same end of the separation region and a reflector at the other end.

A fourth embodiment, illustrated in the schematic cross-sectional view of FIG. 6, allows the input and output to be arranged on the same end of the electron analyzer. The analyzer is similar to that of FIG. 1 by including the low-pass input reflector 50 on one end of an energy separator 90. However, a second reflector 92 is positioned on the other end of the energy separator 90 and includes a grounded grid 94 and an electrode 96 biased by a power supply 98 to the same negative voltage $-V_B$ as the input reflector 50 or a somewhat larger voltage. The two power supplies 56, 98 may be combined. When the low-energy electrons traveling to the right along the helical path 32 enter the second reflector 50, they are reflected in the opposite direction and reenter the separation region 14 with a polar angle θ that has been reversed but the azimuthal angle φ continues to accumulate when viewed along the initial coordinates as they follow a reverse helical path 100. As a result, when they exit the separation space 14 through the grounded input grid 16, they have a polar angle π-θ, as viewed in the original coordinates and a differential azimuthal angle Δφ dependent upon their energy which has accumulated along a double pass through the energy separator 90.

The beam optics 36 and imaging screen 38 are arranged on the input end of energy separator 90 and operate similarly to the previously described embodiments. It is possible to avoid interference between the input reflector 50 and beam optics 36 since only the low-energy electrons are exiting the energy separator 90. Therefore, only a limited azimuthal range Δφ is being analyzed, and the reflector 50 and optics 36 can be arranged at different azimuthal angles about the analyzer axis 26. It is possible to eliminate the separate magnetic exit grid 18 by making the grounded grid 94 of a magnetic material so that it terminates the magnetic field in the separation region 14 and shunts it to the magnetic yoke 20.

The description of the embodiment of FIG. 6 does not include many of the complexities and improvements described with reference to the other embodiments, but the various embodiments may be combined to enjoy the benefits of each of them.

The reflector 92 of FIG. 6 can be advantageously applied to the prior art electron analyzer of FIG. 1 to allow input and extraction from the same end of analyzer 10. Furthermore, it is possible to remove the low-pass reflector 50 of FIG. 6 on the input side and to incline the input beam 24 at a polar angle with respect to the central axis 26. Instead the reflector 92 on the other side of the separation region 14 when biased at the low-pass energy $eV_B$ acts as the low-pass filter.

It is also appreciated that the input beam 24 of FIG. 6, the reflector 50, and the imaging elements 36, 38 may be arranged at slightly different positions and orientations so that the input beam 24 enters the analyzing region 14 at a polar angle θ without being filtered and that the low-pass reflector 50 instead analyzes the output beam before it is imaged. Low-pass filtering of the output beam prior to imaging can be applied to the other embodiments as well. It thus becomes apparent that the combination of the low-pass reflector and the energy separator may be arranged nearly arbitrarily along the transport path of the electrons between the input beam and the imaging optics. Putting the low-pass reflector on the input side eliminates the high-energy electrons from the separation region, but the other designs may simplify the overall construction.

The invention simplifies the detection of small, low-energy components of a wide spectrum of electron energies with only minimal increase in the complexity of the apparatus.

What is claimed is:

1. An electron energy analyzer with a low-pass filter and an electron reflector comprising:

an electron energy analyzer having a drift region and a magnetic field extending along a central axis, electrons being analyzed rotating around said magnetic field and accumulating an amount of rotation dependent upon their energy;

a low-pass first electron reflector comprising a first mesh held at a first electrical potential and an electrode disposed on a side of said first mesh opposite on input side of said drift region, separated from said first mesh by a gap, and held at a second electrical potential more positive than said first electrical potential, said first mesh and said electrode having generally respective surfaces inclined to said central axis; and a source of electrons irradiating electrons toward said reflector at an angle such that electrons reflected from said reflector are incident upon said drift region at angles inclined to said central axis.

2. The analyzer of claim 1, wherein said electron energy analyzer comprises:

a magnetic field generator producing a generally axial magnetic field along said central axis;

a first magnetically field terminating mesh disposed on said input side of said drift region and held at said first electrical potential; and a second magnetically field terminating mesh disposed on an output side of said drift region.

3. The analyzer of claim 1, further comprising:
optics positioned on an output side of said drift region opposite said input side; and
an imaging detector receiving the focused output of said optics.

4. The analyzer of claim 1, further comprising:
a second electron reflector positioned on a side of said drift region opposite said input side;
optics positioned on said input side of said drift region receiving electrons reflected by said second electron reflector and exiting said drift region on said input side; and
an imaging detector receiving the focused output of said optics.

5. The analyzer of claim 4, wherein said second electron reflector is disposed in said drift region.

6. The analyzer of claim 1, wherein said first mesh and said electrode are flat and parallel.

7. The analyzer of claim 1, wherein said first mesh and said electrode are curved in only one dimension.

8. The analyzer of claim 1, wherein said first mesh and said electrode are curved in two dimensions.

9. The analyzer of claim 1, wherein said first mesh and said electrode are curved and separated by a sufficiently large gap to provide chromatic dispersion to electrons reflected by said electron reflector.

10. An electron energy analyzer with a low-pass filter, comprising:
an electron energy analyzer having a drift region and a magnetic field extending along a central axis of said drift region, electrons being analyzed rotating around said magnetic field and accumulating an amount of rotation dependent upon their energy;
a low-pass first electron reflector disposed at first end of said drift region comprising a first mesh held at a first electrical potential and an electrode disposed on a side of said first mesh opposite drift region, separated from said first mesh by a gap, and held at a second electrical potential more positive than said first electrical potential;
a source of electrons irradiating electrons toward one of said drift region and said reflector; and
an electron imaging system receiving said electrons after they have exited said drift region.

11. The analyzer of claim 10, wherein source of electrons is disposed on said first end of said reflector and irradiates said reflector with said electrons and said imaging system is disposed on a second end of said drift region opposite said first end.

12. The analyzer of claim 10, wherein said source of electrons is disposed on a second end of said drift region and irradiates said drift region with said electrons at an angle offset from said central axis.

13. The analyzer of claim 12, wherein said reflector reflects said electrons back along said central axis and wherein said imaging system is disposed on said first end of said drift region.

14. The analyzer of claim 13, wherein said reflector system obliquely reflects said electrons toward said imaging system disposed on said second end of said drift region.

15. An electron analyzer, comprising:
an electron analyzer having a drift region and a magnetic field extending along a central axis, electrons being analyzed rotating around said magnetic field and accumulating an amount of rotation dependent upon their energy;
a source of electrons irradiation electrons toward a first end of said drift region and an angle offset with respect to said central axis;
an electron reflector disposed at a second end of said drift region; and
an electron detection system disposed at said first end of said drift region to detect angular trajectories of electrons exiting said drift region from said first end thereof after being reflected by said electron reflector.

16. The analyzer of claim 15, wherein said electron reflector comprises a grid held at a first predetermined potential and an electrode positioned on a side of said grid opposite said drift region and held at a second predetermined potential more negative than said first predetermined potential.

17. The electron analyzer of claim 1 further comprising an electron detector that detects at different positions electrons having different energies, the different positions being determined by the amount of rotation accumulated in the electron energy analyzer.

18. The electron analyzer of claim 1 in which the electron analyzer passes electrons having different energies, the angle at which each electrons leaves the analyzer being determined by the energy of that electron.

* * * * *